(12) United States Patent
Kojima et al.

(10) Patent No.: US 9,834,796 B2
(45) Date of Patent: Dec. 5, 2017

(54) METHOD FOR PRODUCING USEFUL METABOLITE FROM FILAMENTOUS FUNGUS

(75) Inventors: Masanobu Kojima, Nagano (JP); Hiroshi Fujii, Nagano (JP)

(73) Assignee: Shinshu University, Nagano (JP)

( * ) Notice: Subject to any disclaimer, the term of this patent is extended or adjusted under 35 U.S.C. 154(b) by 130 days.

(21) Appl. No.: 14/343,404

(22) PCT Filed: Aug. 6, 2012

(86) PCT No.: PCT/JP2012/070017
§ 371 (c)(1), (2), (4) Date: May 21, 2014

(87) PCT Pub. No.: WO2013/035473
PCT Pub. Date: Mar. 14, 2013

(65) Prior Publication Data
US 2014/0332719 A1    Nov. 13, 2014

(30) Foreign Application Priority Data

Sep. 7, 2011 (JP) ................. 2011-194491

(51) Int. Cl.
*C12P 7/42* (2006.01)
*C12N 1/14* (2006.01)
*C12N 13/00* (2006.01)

(52) U.S. Cl.
CPC ............... *C12P 7/42* (2013.01); *C12N 1/14* (2013.01); *C12N 13/00* (2013.01)

(58) Field of Classification Search
None
See application file for complete search history.

(56) References Cited

U.S. PATENT DOCUMENTS

| | | | |
|---|---|---|---|
| 6,130,354 A | 10/2000 | Mair | |
| 8,435,769 B2 * | 5/2013 | Bogosian | C12P 7/42 435/146 |
| 9,284,566 B2 * | 3/2016 | Liao | C12N 1/20 |
| 2001/0036653 A1 | 11/2001 | Inding et al. | |
| 2002/0006960 A1 | 1/2002 | Abrecht et al. | |
| 2010/0239711 A1 * | 9/2010 | Li | A23F 5/02 426/45 |
| 2011/0020885 A1 * | 1/2011 | Bogosian | C12P 7/42 435/146 |
| 2014/0332719 A1 * | 11/2014 | Kojima | C12P 7/42 252/182.31 |

FOREIGN PATENT DOCUMENTS

| | | | |
|---|---|---|---|
| CN | 101134958 A | | 3/2008 |
| CN | 101857879 A | | 10/2010 |
| EP | 1092766 A1 * | | 4/2001 |
| JP | 55088699 A | | 7/1980 |
| JP | 07227289 A | | 8/1995 |
| JP | 11152230 A | | 6/1999 |
| JP | 11349583 A | | 12/1999 |
| JP | 200078967 A | | 3/2000 |
| JP | 2001288152 A | | 10/2001 |
| JP | 2001354635 A | | 12/2001 |
| JP | 2002281993 A | | 10/2002 |
| JP | 3641384 B2 | | 1/2005 |
| JP | 2007300809 A | | 11/2007 |
| JP | 2009201473 A | | 9/2009 |

OTHER PUBLICATIONS

Raghavendra et al, Prospectingfor alternate sources of shikimic acid, a precursor of Tamiflu, a bird-flu drug, Current Science, 2009, 96/6:771-772.*
Calvo et al, Microbiology and Molecular Biology Reviews, Sep. 2002, p. 447-459 vol. 66, No. 3.*
Ghosh et al, Biotechnology Advances 30 (2012) 1425-1431.*
Hawkins et al, J. General Microbiology, 1993, 139:2891-2899.*
Ikeda, Appl. Microbiol. Biotechnol., 2006, 69:615-626.*
Kojima, M. Kimura, N. & Miura, R. Regulation of Primary Metabolic Pathways in Oyster Mushroom Mycelia Induced by Blue Light Stimulation: Accumulation of Shikimic Acid. Sci. Rep. 5, 8630; DOI:10.1038/srep08630 (2015).*
Kramer et al, Metabolic Engineering, 2003, 5:277-283.*
Nakano et al, Biosci. Biotechnol. Biochem., 74 (10), 2160-2165, 2010.*
Stocker-Worgotter, Nat. Prod. Rep., 2008, 25, 188-200.*
Farina et al, Angew. Chem. Int. Ed., 2006, 45:7330-7334.*
Mani et al, Can. J. Bot., 1982, 60:549-553.*
Bongaerts et al, Metabolic Engineering 3, 289-300 (2001).*
Gregori et al, Food Technol. Biotechnol., 2007, 45/3:238-249.*
Nakano et al, J. Light and Visual Environment, 2011, 35/1:90-94.*
B.A. Bohm, "Shikimic Acid," Chemical Reviews, vol. 65, pp. 435-466 (1965).
Y. Nakano, et al., "Identification of Blue-Light Photresponse Genes in Oyster Mushroom *Mycelia*," Biosci. Biotechnol. Biochem., 74 (10), 2160-2165, 2010.
M. Kojima, et al., "Correlation Between Gene Expression and Metabolite Production in Oyster Mushroom *Mycelia* Stimulated by Blue Light," Meeting Abstract, Sep. 2011.
M. Dawoud, et al., "Evaluation of Nutritional Substrate and Physical Stress (Gamma Irradiation) in B-Glucan Productivity by Mushroom (*Pleurotus ostreatus*)," African Journal of Biotechnology, vol. 10 (69), pp. 15578-15586, Nov. 7, 2011.
A. Gregori, et al., "Cultivation Techniques and Medicinal Properties of *Pleurotus* spp.," Food Technol. Biotechnol., vol. 45 (3), pp. 238-249 (2007).

(Continued)

*Primary Examiner* — Nita M. Minnifield
(74) *Attorney, Agent, or Firm* — Foley & Lardner LLP

(57) ABSTRACT

The present invention relates to a method for producing useful metabolites such as shikimic acid from filamentous fungus. The useful metabolites can be produced by a production method involving a step of inhibiting the growth of the filamentous fungus, specifically by applying a stimulus of light having a center wavelength shorter than 570 nm to the filamentous fungus, to increase the content of the useful metabolite in a hypha of the filamentous fungus.

6 Claims, 5 Drawing Sheets

(56) References Cited

OTHER PUBLICATIONS

Project Information, Shinshu University, pp. 1-24. XP-002734176.

Y. Nakano, et al., "Effects of Light Wavelength and Intensity on the Expression of Photoresponse Genes in Oyster Mushroom *Mycelia*," J. Light & Vis. Env., vol. 35, No. 1, 2011, pp. 90-94.

N. Poyedinok, et al., "The Activity of Certain Medicinal Mushrooms After Light Influences," International Journal of Medicinal Mushrooms, vol. 9, pp. 342-343, (2007).

M. Chen, et al., "Anticancer Activities of Wild and Cultivated Edible Danish Mushroom," International Journal of Medicinal Mushrooms, vol. 9, pp. 290-291, (2007).

Y. Miyazaki, et al., "Light-Stimulative Effects on the Cultivation of Edible Mushrooms by Using Blue LED," Proceedsings of 7th Int'l. Conference on Mushroom Biology and Mushroom Products (ICMBMP7) 2011.

Avagyan, et al., "Change of Metabolic Activity of Pleurotus Ostreatus Culture Under the Influence of Electromagnetic Waves," (translated) Mikologiya I Fitopatologiya, vol. 45, Nov. 2011, pp. 77-83.

European Search Report dated Jan. 21, 2015 corresponding to European Application No. 12 82 9534.

\* cited by examiner

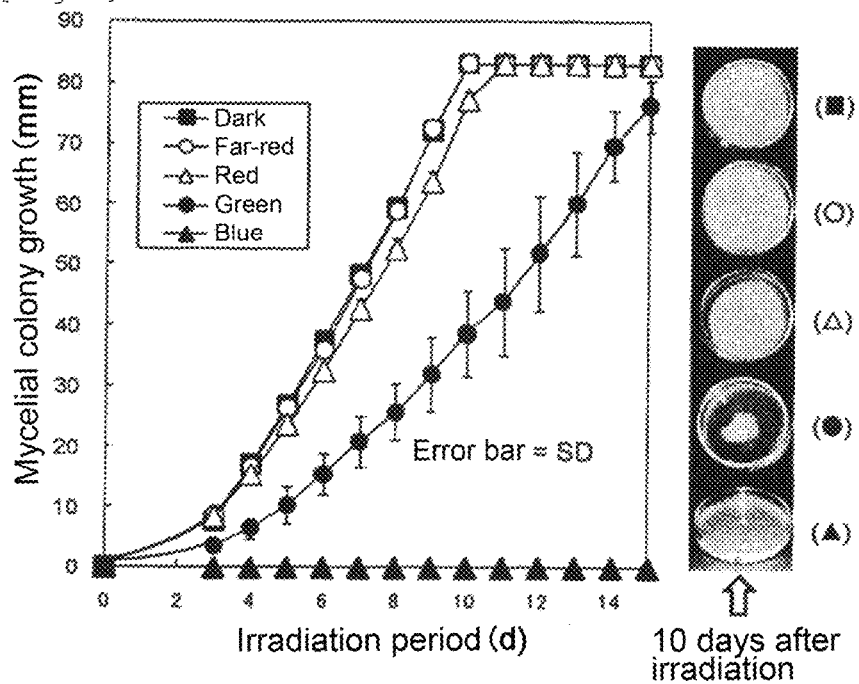
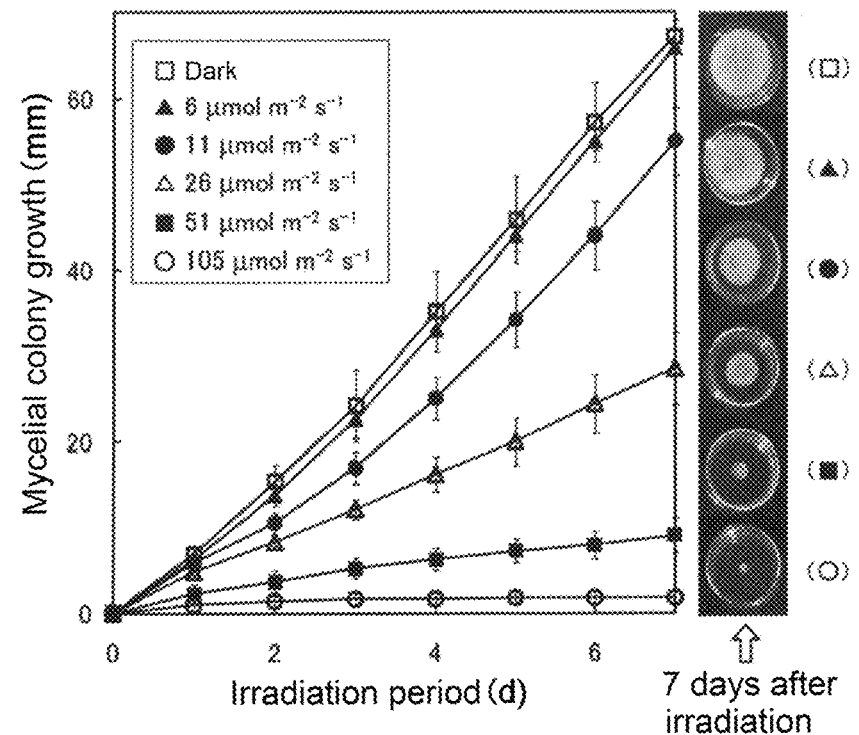

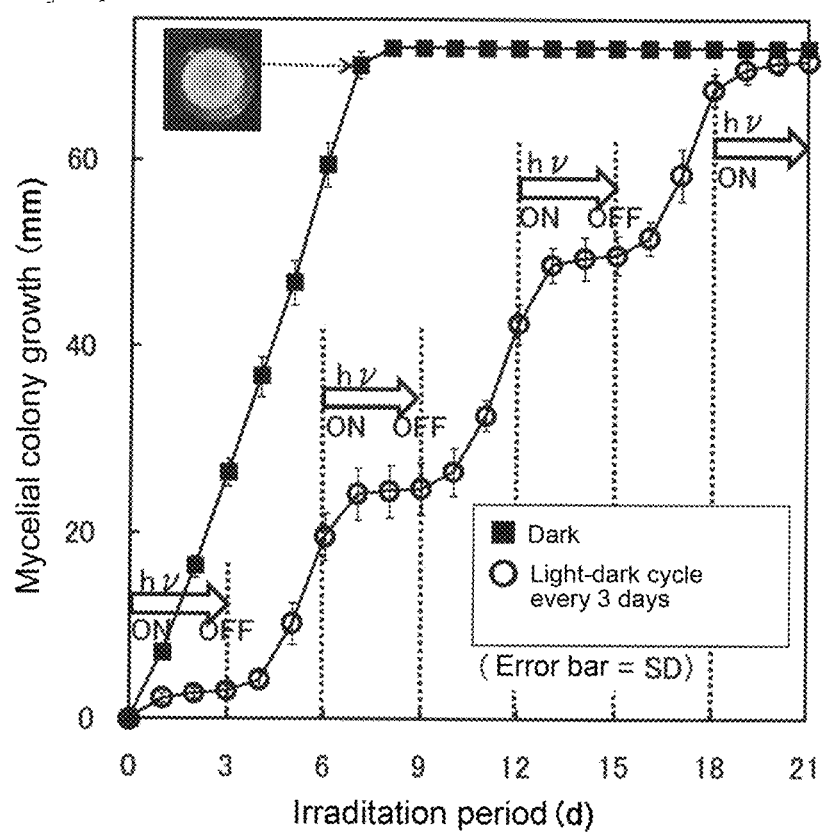

[Fig.4]
A. Control (100% EtOH)   B. Sample (0h-0.2%)
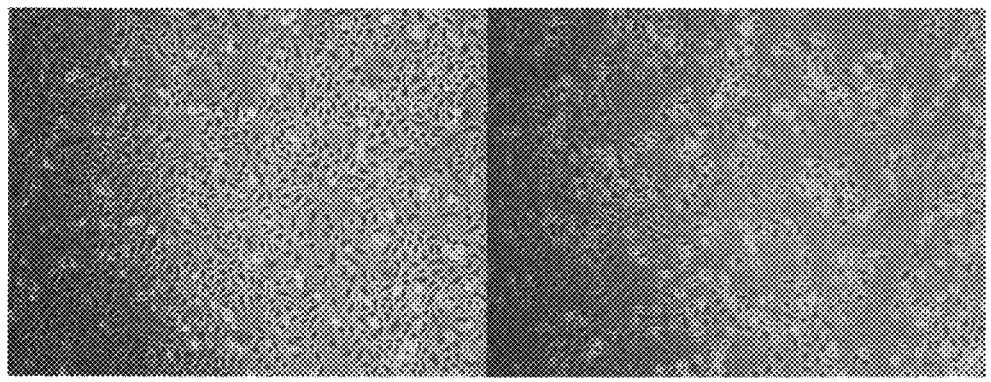
C. Sample (0h-2%)   D. Sample (48h-0.2%)
E. Sample (48h-2%)
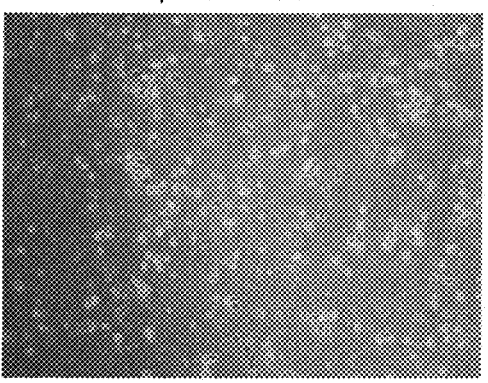

[Fig.5]
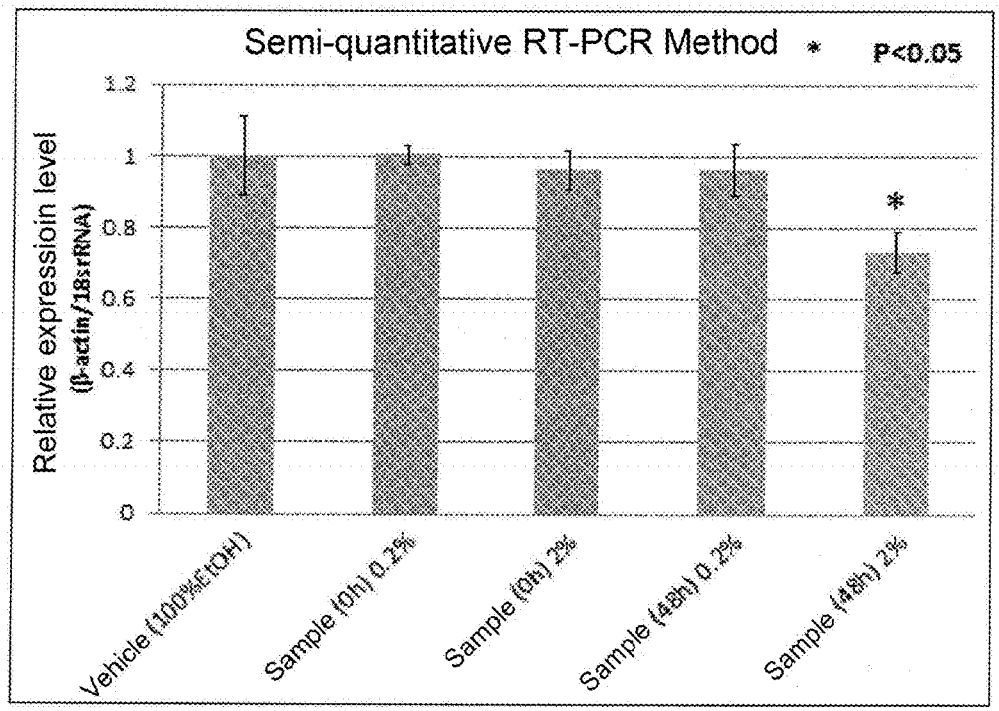
[Fig.6]
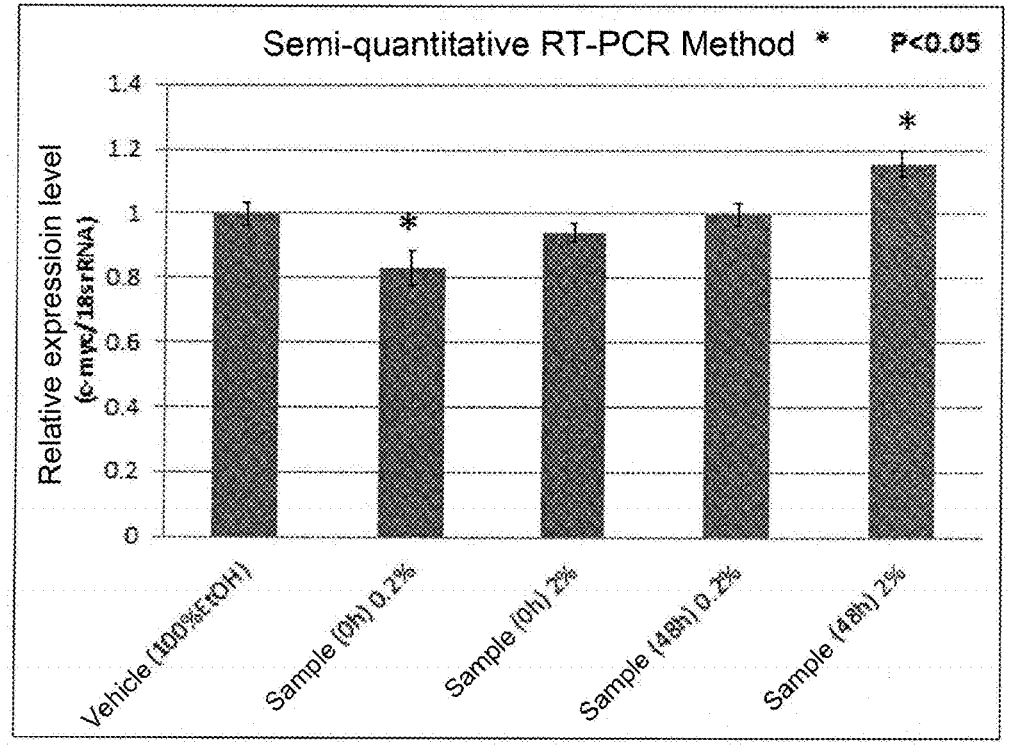

[Fig. 7]
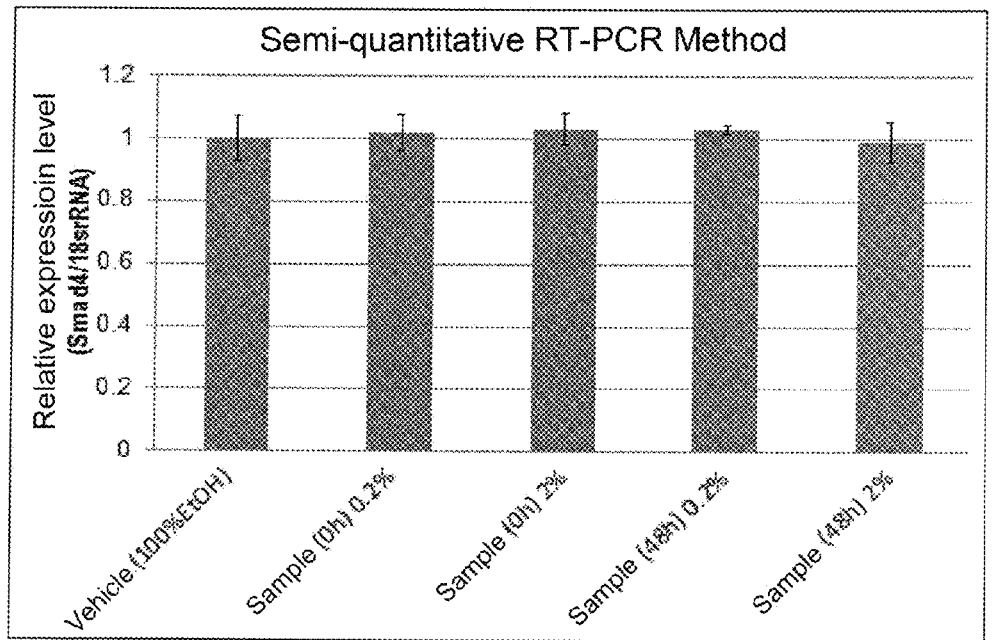
[Fig. 8]
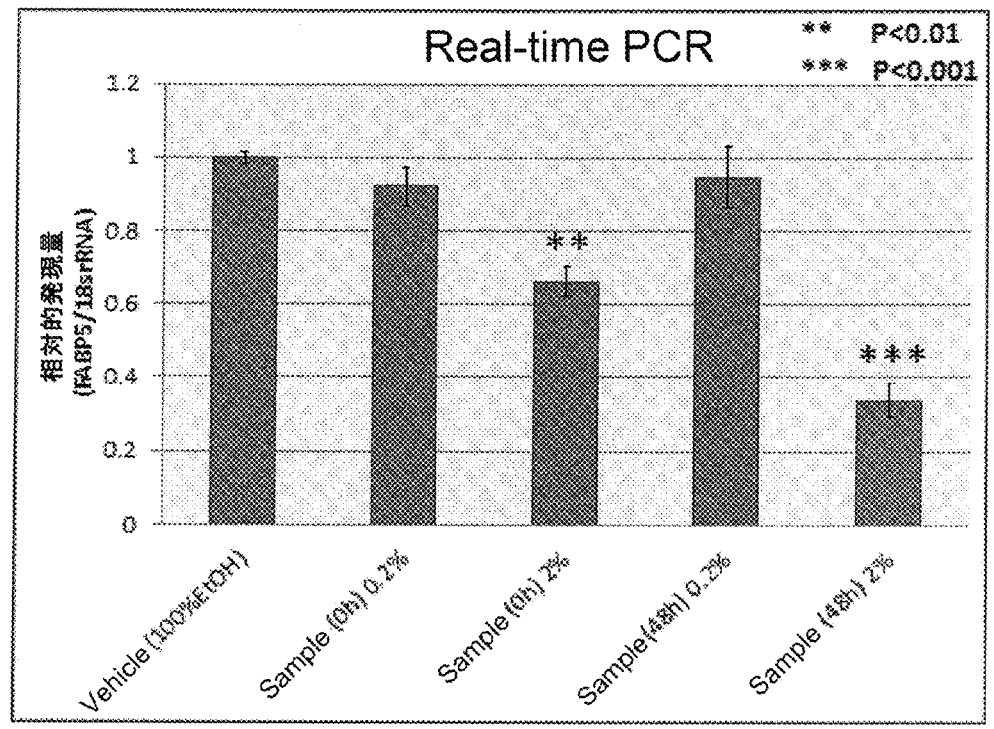

```
                         SEQUENCE LISTING

<160> NUMBER OF SEQ ID NOS: 12

<210> SEQ ID NO 1
<211> LENGTH: 20
<212> TYPE: DNA
<213> ORGANISM: Artificial
<220> FEATURE:
<223> OTHER INFORMATION: semi-quantitative RT-PCR primer

<400> SEQUENCE: 1
aaacggctac cacatccaag                                                  20

<210> SEQ ID NO 2
<211> LENGTH: 20
<212> TYPE: DNA
<213> ORGANISM: Artificial
<220> FEATURE:
<223> OTHER INFORMATION: semi-quantitative RT-PCR primer

<400> SEQUENCE: 2
cctccaatgg atcctcgtta                                                  20

<210> SEQ ID NO 3
<211> LENGTH: 20
<212> TYPE: DNA
<213> ORGANISM: Artificial
<220> FEATURE:
<223> OTHER INFORMATION: semi-quantitative RT-PCR primer

<400> SEQUENCE: 3
aggtcatcac cattggcaat                                                  20

<210> SEQ ID NO 4
<211> LENGTH: 20
<212> TYPE: DNA
<213> ORGANISM: Artificial
<220> FEATURE:
<223> OTHER INFORMATION: semi-quantitative RT-PCR primer

<400> SEQUENCE: 4
actcgtcata ctcctgcttg                                                  20

<210> SEQ ID NO 5
<211> LENGTH: 20
<212> TYPE: DNA
<213> ORGANISM: Artificial
<220> FEATURE:
<223> OTHER INFORMATION: semi-quantitative RT-PCR primer

<400> SEQUENCE: 5
ttgcttccac ttgaatgctg                                                  20

<210> SEQ ID NO 6
<211> LENGTH: 20
<212> TYPE: DNA
<213> ORGANISM: Artificial
<220> FEATURE:
<223> OTHER INFORMATION: semi-quantitative RT-PCR primer
```

-continued

<400> SEQUENCE: 6
cttcaaaggg gacaccaaaa                                              20

<210> SEQ ID NO 7
<211> LENGTH: 20
<212> TYPE: DNA
<213> ORGANISM: Artificial
<220> FEATURE:
<223> OTHER INFORMATION: semi-quantitative RT-PCR primer

<400> SEQUENCE: 7
ttcgggtagt ggaaaaccag                                              20

<210> SEQ ID NO 8
<211> LENGTH: 20
<212> TYPE: DNA
<213> ORGANISM: Artificial
<220> FEATURE:
<223> OTHER INFORMATION: semi-quantitative RT-PCR primer

<400> SEQUENCE: 8
cagcagctcg aatttcttcc                                              20

<210> SEQ ID NO 9
<211> LENGTH: 20
<212> TYPE: DNA
<213> ORGANISM: Artificial
<220> FEATURE:
<223> OTHER INFORMATION: real time PCR primer

<400> SEQUENCE: 9
cggctaccac atccaaggaa                                              20

<210> SEQ ID NO 10
<211> LENGTH: 18
<212> TYPE: DNA
<213> ORGANISM: Artificial
<220> FEATURE:
<223> OTHER INFORMATION: real time PCR primer

<400> SEQUENCE: 10
gctggaatta ccgcggct                                                18

<210> SEQ ID NO 11
<211> LENGTH: 22
<212> TYPE: DNA
<213> ORGANISM: Artificial
<220> FEATURE:
<223> OTHER INFORMATION: real time PCR primer

<400> SEQUENCE: 11
gctgatggca gaaaaactca ga                                           22

<210> SEQ ID NO 12
<211> LENGTH: 20
<212> TYPE: DNA
<213> ORGANISM: Artificial
<220> FEATURE:
<223> OTHER INFORMATION: real time PCR primer

<400> SEQUENCE: 12
cctgatgctg aaccaatgca                                              20

US 9,834,796 B2

METHOD FOR PRODUCING USEFUL METABOLITE FROM FILAMENTOUS FUNGUS

RELATED APPLICATION

This application is a national stage filing under 35 U.S.C. §371 of international application PCT/JP2012/070017, filed Aug. 6, 2012, the disclosure of which is incorporated by reference herein in its entirety.

TECHNICAL FIELD

The present invention relates to a method for producing useful metabolites from filamentous fungi. More precisely, the present invention relates to a method for increasing the content of metabolites such as shikimic acid in mycelia by applying a stimulus with light of specific wavelength in the cultivation of filamentous fungi.

BACKGROUND ART

Shikimic acid is a common biosynthetic intermediate of various aromatic compounds in plants and microorganisms, and is a very important substance to plants and microorganisms. Further, shikimic acid is a very useful compound used as a raw material for manufacturing Oseltamivir (TAMIFLU) (registered trademark), a medicine to treat new strains of influenza, as well as a lot of medicines and agricultural chemicals.

Currently, shikimic acid is mainly produced by extracting and purifying from *Illicium verum* (star anise). However, due to a problem that the content of component is not constant in the case of extracting from natural products, methods for stably producing shikimic acid still have been pursued. For example, as synthetic production approaches, a method for preparing shikimic acid derivatives by selective dehydration from quinic acid using Vilsmeier reagent (Patent Publication 1), a method for producing diaminoshikimic acid from isophthalic acid(Patent Publication 2), and a method for preparing diaminoshikimic acid from furan (Patent Publication 3), etc. have been reported. All of these methods are the methods for producing shikimic acid derivatives and further step(s) is (are) required to obtain target shikimic acid.

In addition, as other production methods from quinic acid, a method for producing shikimic acid in two steps by using shikimic acid dehydrogenase and glucose dehydrogenase derived from an acetobactor (Patent Publication 4) and a method converting quinic acid to an acetal of quinic acid ester followed by producing shikimic acid from the acetal (Patent Publication 5), etc. have been reported. As production methods using microorganisms, the methods utilizing a Citrobacter microorganism (Patent Publication 6 and 7), etc. have been reported; further, a method for producing shikimic acid by using chlorogenic acid contained in coffee grounds as a raw material together with a microorganism that has chlorogenic acid hydrolase as a microbial catalyst (Patent Publication 8), etc. has been reported. Moreover, as a production method of shikimic acid by fermentation using *E. coli* has been reported (Non-patent Publication 1).

On the other hand, the inventors of the present invention so far have reported that the mycelial growth of *Pleurotus ostreatus*, a type of basidiomycetes, is suppressed by blue light, and also that gene expression response to blue light is observed (Non-patent Publication 2 and 3). However, it is totally unknown what kinds of metabolites are produced, when *Pleurotus ostreatus* is stimulated by blue light and the growth thereof is suppressed.

PRIOR ART DOCUMENTS

Reference List

Patent Publication 1: JP 3641384 B
Patent Publication 2: JP 2001-354635 A
Patent Publication 3: JP 2001-288152 A
Patent Publication 4: JP 2007-300809 A
Patent Publication 5: JP H11-349583 A
Patent Publication 6: JP 2000-078967 A
Patent Publication 7: JP 2002-281993 A
Patent Publication 8: JP 2009-201473 A
Non-patent Publication 1: B. A.Bohm, Chemical Reviews, 65, 435-466 (1965)
Non-patent Publication 2: Nakano et al., Biosci Biotechnol Biochem. 2010; 74(10): 2160-5.
Non-patent Publication 3: Nakano et al., J. Light & Vis. Env.; 35(1): 90-94 2011

SUMMARY OF THE INVENTION

Problems to Be Solved by the Invention

Since all of the conventional methods for producing shikimic acid require several steps for the production, there is a problem that the conventional methods are not suitable for mass production because the conventional methods need a lot of time and cost for production. In forging ahead with research to solve the problem, the present inventors have found that useful metabolites are produced by stimulating filamentous fungi with light, e.g., a stimulation of filamentous fungi such as *Pleurotus ostreatus* with blue light dramatically increases the content of shikimic acid in the mycelia and the extracts in the organic layer from the mycelia stimulated by blue light shows antitumor activity, and as a result of further investigation, the present invention has been accomplished.

Means for Solving the Problems

The present invention relates to useful metabolites of filamentous fungi and a method for producing the useful metabolites as follows.

[1] A method for producing useful metabolites comprising a growth suppression process that increases the content of useful metabolites in mycelia by suppressing the growth of filamentous fungi.

[2] The method for producing useful metabolites of [1], wherein the growth suppression process is the suppression of the growth of filamentous fungi by applying stimulus of light having a center wavelength shorter than 570 nm to the filamentous fungi.

[3] The method of [1] or [2], wherein the method comprises a process of extracting useful metabolites from filamentous fungi.

[4] The method of any one of [1] to [3], wherein the filamentous fungi are basidiomycetes.

[5] The method of [4], wherein the basidiomycete is genus *Pleurotus*.

[6] The method of any one of [2] to [5], wherein the stimulus of light is blue-light stimulation.

[7] The method of any one of [2] to [6], wherein the stimulus of light is applied with irradiation at the light intensity more than 10 μmol m$^{-2}$ s$^{-1}$.

[8] The method of any one of [2] to [7], wherein the stimulus of light is applied with intermittent irradiation.

[9] The method of any one of [1] to [8], wherein the useful metabolite is shikimic acid.

[10] The method of any one of [1] to [8], wherein the useful metabolite is an antitumor substance.

[11] A useful metabolite produced by the method of any one of [1] to [10].

Effects of the Invention

The method for producing useful metabolites of the present invention makes it possible to produce physiologically active substances used in medicines or precursors as raw materials of medicines from filamentous fungi efficiently. For example, the present invention makes it possible to produce shikimic acid from filamentous fungi efficiently.

The method for producing shikimic acid of the present invention makes it possible to dramatically increase the content of shikimic acid and accumulate it in mycelia of the filamentous fungi by only one-step process. According to the method of the present invention, shikimic acid can be obtained efficiently by using commercially available and inexpensive materials, thus it is possible to produce shikimic acid at low cost and short times, and shikimic acid can be provided stably.

The method for producing shikimic acid of the present invention utilizes the suppression mechanism of mycelial growth by light. It is presumed that when light stimulation is applied to filamentous fungi cultured in the dark, the biosynthetic pathway of aromatic amino acids is blocked after shikimic acid is biosynthesized in mycelia; thereby, the shikimic acid accumulates and due to which the content of shikimic acid can be increased dramatically.

Further, it is possible to get novel products by using the obtained shikimic acid as a starting material. Namely, the blocking of the biosynthetic pathway of aromatic amino acids of the present invention would make it possible not only to obtain shikimic acid but also to provide means for obtaining other substances synthesized from shikimic acid as a precursor by adding processes further reacting with shikimic acid. By applying these synthesized substances to medicines, the present invention can contribute to the medical field.

Furthermore, the method for producing useful metabolites of the present invention makes it possible to produce physiologically active substance such as antitumor substances. The antitumor substance produced by the present invention can effectively suppress the gene expression coding FABP5 related to cancer metastasis; in addition, the antitumor substance shows a high antitumor effect even at a small amount, and thus is possible to provide a safe antitumor agent.

BRIEF DESCRIPTION OF DRAWINGS

FIG. 1 is a graph showing the relation between the wavelength of irradiation light and the growth of *Pleurotus ostreatus* mycelia.

FIG. 2 is a graph showing the relation between the intensity of blue light irradiated and the growth of *Pleurotus ostreatus* mycelia.

FIG. 3 is a graph showing change in the growth of *Pleurotus ostreatus* mycelia when blue-light irradiation was carried out intermittently.

FIG. 4 is a picture showing a result of the observation of cell number affected by the addition of components from organic layer.

FIG. 5 is a graph showing an analysis result of the gene expression coding β-actin by a semi-quantitative PCR method.

FIG. 6 is a graph showing an analysis result of the gene expression coding c-myc by a semi-quantitative PCR method.

FIG. 7 is a graph showing an analysis result of the gene expression coding Smad4 by a semi-quantitative PCR method.

FIG. 8 is a graph showing an analysis result of the gene expression coding FABP5 by a semi-quantitative PCR method.

MODE FOR CARRYING OUT THE INVENTION

As a filamentous fungus used in the process for producing useful metabolites of the present invention, basidiomycetes, ascomycetes, zygomycetes, and myxomycetes, etc. can be utilized. Basidiomycetes are particularly preferable. Basidiomycetes include genus *Pleurotus* and genus *Lentinula*, etc., and specifically include *Pleurotus ostreatus, Pleurotus eryngii*, and *Lentinula edodes*, etc. As a basidiomycete used in the present invention, genus *Pleurotus* is preferable, and *Pleurotus ostreatus* is particularly preferable.

The method for producing useful metabolites of the present invention may comprise a growth suppression process that increases the content of useful metabolites in mycelia by suppressing the growth of filamentous fungi. Preferably, the growth suppression process is the suppression of the growth of filamentous fungi by applying light stimulation.

As for the light stimulation, monochromatic visible light are preferable, which include violet, blue-violet, blue, blue-green, green, and yellow-green visible lights, preferably blue light. It may also be near-ultraviolet (e.g., UVA).

It may comprise a culture process of performing filamentous fungi culture before light irradiation. The state of filamentous fungi when light stimulation applied is not particularly limited and it is applicable to both mycelia and fruit bodies; the culture time can be shortened when utilizing mycelia.

As for the wavelength of light, a center wavelength is desirably shorter than 570 nm, preferably 400-545 nm, more preferably 450-495 nm, and further preferably 460-480 nm. Alternatively, it may be 315-400 nm.

Photon flux density is desirably not less than 10 μmol m$^{-2}$ s$^{-1}$, and it maybe 10-1000 μmol m$^{-2}$ s$^{-1}$, but not limited thereto. It is preferably 30-500 μmol m$^{-2}$s$^{-1}$, more preferably 50-200 μmol m$^{-2}$s$^{-1}$, and further preferably 90-120 μmol m$^{-2}$ s$^{-1}$.

Irradiation time is not limited particularly, but desirably not less than 3 hours for single irradiation. It is preferably 12-120 hours, and more preferably 24-60 hours. Further, irradiation is preferably carried out continuously, but dark culture and light culture (irradiation) maybe repeated in turn. For example, dark culture and light culture (irradiation) may be repeated every 1, 2, 3, 4, or 5 day(s).

As a light irradiation device, a device generating light to stimulate, such as monochromatic visible light and near-ultraviolet, may be used without limitation. For example, an LED light irradiation device may be used.

The method for producing useful metabolites of the present invention may comprise a process of extracting useful metabolites from the filamentous fungi. The extracts may be extracted by a method of separating into an organic layer and a water layer by using an organic solvent. As for the extracting solvent for metabolites, methanol, water, chloroform, and dichloromethane, etc. maybe used, but not limited thereto. In addition, the organic solvent, e.g., esters such as methyl acetate and ethyl acetate, ketones such as acetone, ethers such as diethyl ether, aromatic hydrocarbons such as xylene, toluene, and benzene, and aliphatic hydrocarbons such as hexane, as well as alcohols such as methanol, ethanol, isopropanol, and butanol may also be used in combination. Typically, the antitumor substance is highly contained in the organic layer, while shikimic acid is highly contained in the water layer.

As for the method for extracting useful metabolites of the present invention, e.g., methanol, chloroform, and water may be used as the solvents. Specifically, after adding methanol and homogenizing mycelia, equal amount of chloroform to methanol and ⅖ amount of water to methanol are added, centrifugal separation etc. is performed, and separation into the water layer and the organic layeris achieved. The obtained water layer and organic layer may be subjected to further centrifugal separation and ultrafiltration, etc. Typically, useful metabolites such as shikimic acid can be collected from the water layer, and the antitumor substance of the present invention can be collected from the organic layer.

Therefore, the method for producing useful metabolites of the present invention may comprise a process of extracting useful metabolites comprising a process of homogenizing mycelia, a process of centrifugal separation, and a process of extraction using organic solvents and a process of purification such as separation and drying.

The useful metabolites of the present invention include primary metabolite and secondary metabolite; the metabolites include an intermediate of aromatic compounds such as shikimic acid and physiologically active substances such as an antitumor substance, etc.

One aspect of the present invention relates to a method for producing shikimic acid.

In one embodiment of the present invention, the method for producing shikimic acid of the present invention is characterized by having a growth suppression process that increases the content of shikimic acid in mycelia by suppressing the growth of filamentous fungi.

Further, it is characterized in that the filamentous fungus is a mycelium.

Moreover, the growth suppression process is characterized in that the growth of filamentous fungi is suppressed by applying light stimulation to filamentous fungi.

Moreover, it is characterized in that the light used for light stimulation is light with a wavelength shorter than 570 nm.

Moreover, it is characterized in that the light used for light stimulation is blue light.

Moreover, it is characterized in that a culture process conducting a culture of the filamentous fungi is comprised as the pre-process of the growth suppression process.

The method for producing shikimic acid of the present invention is based on the knowledge that the stimulus of light plays an important role in controlling the growth rate and morphogenesis of plants and fungi, and in increasing the amount of contained functional nutrient ingredients therein; particularly, the mycelial growth is remarkably suppressed when light not more than a specific wavelength is irradiated to the Pleurotus ostreatus mycelia at the vegetative stage.

Further, it is based on the knowledge that this suppression significantly appears when the irradiation light has a wavelength shorter than that of the green light, particularly when the irradiation light is blue light, and that the suppression degree depends on the photon flux density of the irradiation light.

As mentioned above, the method for producing shikimic acid of the present invention utilizes the suppression mechanism of fungi growth by light. It is presumed that after the biosynthesis of shikimic acid in mycelia, shikimic acid accumulates in mycelia by blocking the aromatic amino acid biosynthetic pathway by applying light stimulation to filamentous fungi cultured in the dark, thereby the content of shikimic acid can be increased dramatically.

As the blue light receptors of plants, cryptochrome and phototropin have been found. As for the blue light receptors of fungi, WC1 and WC2 in *Neurospora crassa* of ascomycetes are well studied, and they are considered to be involved in the synthesis of carotenoid and the photoregulation of circadian rhythm. Further, as the homologue genes of WC1 and WC2, dst1 in *Coprinopsis cinerea*, which is classified to basidiomycete as same as *Pleurotus ostreatus*, and madA of Phycomyces in zygomycetes have been reported. Thus, the blue light is considered as light that plays a very important role in biological control system, because genes coding for blue light receptors are widely preserved in plants and fungi. The interruption of aromatic amino acid biosynthetic pathway due to the photoreceptors of fungi or the photoreceptor action, and the growth inhibitory action due to the same, are applicable in the interior or exterior of the present invention as a new constitution of an invention, or a new invention per se.

In the method for producing shikimic acid of the present invention, the fungi that increase the content of shikimic acid are not particularly limited, any fungus having photoreceptor and shikimic acid pathway is applicable. Specifically, *Pleurotus ostreatus, Lentinula edodes*, and other ascomycetes, basidiomycetes, zygomycetes, and myxomycetes, etc. are applicable, but basidiomycetes are preferable. Further, the state of filamentous fungi when light stimulation applied is not particularly limited and it is applicable to both mycelia and fruit bodies. However, mycelia are suitable because the culture time can be shortened when utilizing mycelia.

In the method for producing shikimic acid of the present invention, light sources of the irradiation light are not particularly limited, any light source that can produce light of specific wavelength is applicable. However, LED is suitable because of low power consumption. Further, the wavelength of light is not particularly limited; any light with a wavelength that can obtain growth inhibitory action on fungi is applicable. Specifically, visible light, infrared radiation, ultraviolet radiation, and other electromagnetic waves are applicable; monochromatic visible light and near-ultraviolet radiation are preferable. Furthermore, the growth inhibitory action on fungi may be achieved by the stimulus other than light, e.g., temperature and sound. However, the growth inhibitory action is confirmed from the green light with a wavelength in a range from 495 nm to 570 nm, and the blue light with a wavelength in a range of 380 nm to 495 nm is suitable because the growth inhibitory action is significant under in such an occasion.

One aspect of the present invention relates to a method for producing antitumor substances.

The method for producing antitumor substances of the present invention may comprise a process of extracting useful metabolites from filamentous fungi. The extracts may be extracted by a method of separating into an organic layer and a water layer by using an organic solvent. As for the extracting solvent for metabolites, methanol, water, chloroform, and dichloromethane, etc. maybe used, but not limited thereto. In addition, the organic solvent, e.g., esters such as methyl acetate and ethyl acetate, ketones such as acetone, ethers such as diethyl ether, aromatic hydrocarbons such as xylene, toluene, and benzene, and aliphatic hydrocarbons such as hexane, as well as alcohol such as methanol, ethanol, isopropanol, and butanol may also be used in combination. Typically, the antitumor substance of the present invention can be extracted a lot from the organic layer.

The antitumor substance of the present invention has cancer cell proliferation-inhibiting activity or apoptosis-inducing activity. Further, it can effectively suppress the gene expression coding FABP5 and has an excellent antitumor activity even in a small amount.

EXAMPLES

The method for producing useful metabolites of the present invention is explained in detail in the examples described below, but the scope of the present invention should not be limited by these examples.

Example 1

(Devices Used)

In the present example, the device used for cultivation is an ELUX-1096 LED plant cultivation device (CCS). In the present example, an experiment in which shikimic acid was produced in *Pleurotus ostreatus* was carried out at 20° C. As alight source for irradiating *Pleurotus ostreatus* mycelia, LED light source panel ISL series 305×302 (CCS) was used. For the measurement of emission intensity, LI-250 Light-Meter (LI-COR) was used with LI-190 Quantum Sensor (LI-COR) or by attaching 660/730 nm SKR110 Sensor (PP Systems International).

(Preparation of Inoculation Source Mycelia)

In the center of a modified MA medium (composition: 2% malt extract, 2% glucose, 0.1% peptone) with 2.5% agar concentration prepared in a Pyrex (R) Petri dish (diameter, 90 mm), a commercial strain, *Pleurotus ostreatus* KH-3 (Chikumakasei Co.,ltd.), prepared as the test mycelia was inoculated, set in the dark at 20° C., and incubated. By this operation, the mycelial colony grew concentrically in the Petri dish. From the periphery of the mycelial colony, a disk like colony 6 mm in diameter was cut out by a cork borer, and used as the inoculation source of the present example.

(Preparation of Samples for Light Irradiation)

In the center of a GPY medium (composition: 5% glucose, 2.5% polypeptone, 2.5% yeast extract) with 2.5% agar concentration prepared in a Pyrex (R) Petri dish (diameter, 90mm), the inoculation source prepared as mentioned above was inoculated, set in the dark at 20° C., and incubated. In the experiment of the present example, a colony growing till 6 mm in diameter and a colony growing till 20 mm in diameter were used as samples.

(Experiment Concerning Changes in Light Wavelength)

An experiment for confirming the effect of light wavelength on mycelial growth was performed by changing the wavelength of irradiation light to mycelia. The samples prepared as mentioned above were irradiated by monochromatic lights of each wavelength of blue light, green light, red light, and far-red light with emission intensity of 95 µmolm$^{-2}$ s$^{-1}$, and the growth of each mycelial colony was monitored and compared. The tracking of the growth change was made by an evaluation method, in which the maximum value and minimum value of the diameter of mycelial colony was measured every 24 hours and the average value was calculated and set as the amount of the growth change in mycelial colony. The center wavelength of each monochromatic visible light is 470 nm for blue light, 525 nm for green light, 660 nm for red light, and 735 nm for far-red light.

FIG. 1 is a graph showing the growth change of the samples irradiated with the each monochromatic visible light described above. From this figure, it is recognized that in the samples irradiated with red light and far-red light, the mycelial colony grows in the same rate as those incubated in the dark without light irradiation. Further, it is recognized that in the samples irradiated by green light, the mycelial growth becomes significantly slow, and that the mycelial growth is completely stopped by blue-light irradiation. Accordingly, a growth suppression of *Pleurotus ostreatus* mycelia is verified when the light wavelength is shorter than that of green light, and it is recognized as a particularly remarkable phenomenon in blue light.

(Experiment Concerning Changes in Emission Intensity of Blue Light)

An experiment for verifying the effect of light intensity on mycelial growth was performed by changing the emission intensity of blue light irradiated to mycelia. The samples prepared as mentioned above were incubated for one week with blue-light irradiation at emission intensity set at 6 µmol m$^{-2}$ s$^{-1}$, 11 µmol m$^{-2}$ s$^{-1}$, 26 µmol m$^{-2}$ s$^{-1}$, 51 µmol m$^{-2}$ s$^{-1}$, and 105 µmol m$^{-2}$ s$^{-1}$, and the growth of each mycelial colony was monitored and compared. The evaluation method is the same as the above experiment.

FIG. 2 is a graph showing the growth change of mycelial colony on changing the emission intensity of blue light irradiated. From this figure, it is acknowledged that the growth of mycelial colony is more suppressed when the emission intensity of irradiation blue light becomes stronger. Further, it is recognized that for the sample where emission intensity is 105 µmol m$^{-2}$ s$^{-1}$, the growth is completely interrupted. Furthermore, it is recognized that the growth rate becomes constant and stable after the passage of 3 days from the start of the experiment for all samples. Thus, it is recognized that the suppression effect of mycelial growth by blue-light irradiation depends on the emission intensity of light irradiated and that the suppression effect is continuously stable.

(Experiment of Blue-light Intermittent Irradiation)

An experiment for evaluating the effect on the growth of mycelial colony was performed by intermittent irradiation that repeats blue-light irradiation and dark storage alternately. The samples prepared as mentioned above were irradiated for 3 days by blue light set at 105 µmol m$^{-2}$ s$^{-1}$, after that dark storage was performed for 3 days, and this set was repeated alternately for 21 days. The evaluation method is the same as the above experiment.

FIG. 3 is a graph showing the growth change of mycelial colony caused by repeating blue-light irradiation and dark storage alternately. From this figure, it is recognized that the suppression of the mycelial growth due to light irradiation and the recovery of the growth of the mycelial colony due to the interruption of light irradiation alternately appear when blue-light irradiation and dark storage are repeated alternately every 3 days. It is assumed that this is caused by repeated induction of expression and suppression of genes involved in the growth of *Pleurotus ostreatus* mycelia by transmitting blue-light signals.

(Method for Extracting Shikimic Acid)

Extraction of metabolites contained in mycelia was carried out in order to evaluate the content of shikimic acid in *Pleurotus ostreatus* mycelia grown according to the above-mentioned experiments. The extraction method is as described below.

I. The mycelia on the surface of culture medium, which was grown in the Petri dishes in a predetermined size by the growth suppression experiment due to blue-light irradiation to mycelia, were collected by using a scraper (Sumilon MS-93100 (R), Sumitomo Bakelite Co. ltd.). In the case of the present example, the colony was grown till 60 mm in diameter.

II. 500 μL of methanol solution containing 50 μM of the internal standard material was added to 50 mg of the sample collected in the above Process I under ice cooling, and it is homogenized by using a desktop homogenizer (BMS-M10N21, BMS) at 1500 rpm (120 sec×3 times).

III. 500 μL of chloroform and 200 μL of Milli-Q water were added into the solution homogenized in the above Process II. The obtained solution was stirred, mixed, and then centrifugal separation was performed under the following conditions: 2300×g, 4° C., 120 min.

IV. Among the solution centrifugally separated in the above Process III, only 400 μL of an aqueous solution from the water layer was transferred to ultrafiltration tube (Millipore, Ultrafree-MC UFC3 LCC centrifugal filter unit 5 kD).

V. Ultrafiltration was carried out for the solution transferred in the above Process IV by performing further centrifugal separation under the following conditions: 9100×g, 4° C., 120 min.

VI. The filtrate in the above Process V was dried, dissolved in 25 μL of Milli-Q water again, and it was used as a sample for evaluating mycelia obtained in the growth experiments mentioned above.

(Quantification Analysis of Shikimic Acid)

Shikimic acid contained in each sample prepared by the methods mentioned above was quantitatively analyzed. A capillary electrophoresis time-of-flight mass spectrometer (CE-TOFMS System, Agilent Technologies) was used as the device for analysis, which was set to an anion mode, and analysis for anionic metabolites of each sample was carried out. Following 3 samples were used in the analysis : OM-1 obtained by incubating *Pleurotus ostreatus* in the dark, OM-2 obtained by blue-light irradiation for 12 hours to the similar sample as that of OM-1, and OM-3 obtained by blue-light irradiation for 36 hours in the same way.

TABLE 1

| | Analyte name | | |
|---|---|---|---|
| | OM-1 | OM-2 | OM-3 |
| Content, μg/g | 2.3 | 116 | 460 |

Table 1 shows the result of quantitative analysis carried out according to the method mentioned above. Calculation of the content was performed by multiplying the concentration (nmol/g) measured using CE-TOFMS by 174.15, the molecular weight of the shikimic acid. From the table, it is recognized that the content of shikimic acid in the samples is increased, as the irradiation time of blue light to samples is increased. Thus, it is recognized that the increment of shikimic acid in mycelia of the present invention correlates strongly with the irradiation time of blue-light irradiation.

Further, it is confirmed that the method used in the present invention is effective in increasing the content of shikimic acid in mycelia.

Example 2

(Culture Conditions and Extraction Method of Organic Layer Components)

Using the same method as the extraction method of shikimic acid described in Example 1, organic layer components were extracted from the organic layer.

(The Effect of Extract on Cancer Cell Proliferation)

The effect of the obtained organic layer components on cancer cell proliferation was studied.

Human prostate cancer cell PC-3 (acquired from Japan Health Sciences Foundation) was cultured in a RPMI medium (SIGMA) with 10% FBS (MP Biomedicals) . Using the organic layer components prepared as mentioned above, an analysis for the effect on cell proliferation of PC-3 cells was performed by microscopic observation of the number of the cells (FIG. 4).

The organic layer component extracted from the mycelia cultured in the dark and then under blue-light irradiation (48 h) was dissolved by ethanol (EtOH) and added in the medium at a final concentration of 0.2% (v/v) and 2% (v/v) . After 48-hour cultivation, the number of the cells was observed by a microscope.

As shown in FIG. 4, compared to the control (FIG. 4A), concentration-dependent decrease in the number of the cells was seen with the addition of the extract obtained from the culture in the dark (FIGS. 4B and 4C) . Further, the decrease in the number of the cells was also seen with the addition of the extract from the sample irradiated using blue light, and the cell proliferation depressing effect by the extract obtained from the blue light irradiation culture was significant compared to those in the samples obtained from the culture in the dark (FIGS. and 4E).

(Gene Expression Analysis by Semi-quantitative RT-PCR for Cancer Cells Treated with Extracts)

(1) Preparation for Samples

PC-3 cells was cultured in a 6-well Plate (NUNC (registered trademark: MULTIDISH)) till 50% for each well. The organic layer components prepared as mentioned above were used, and gene expression analysis was performed by semi-quantitative RT-PCR. The organic layer components dissolved by ethanol (EtOH) was added in the medium at a final concentration of 0.2% (v/v) and 2% (v/v), and semi-quantitative PCR analysis was performed after 48-hour cultivation.

After cultivation, the medium was removed; washed by PBS, 500 μL of TRIzol was added and pipetting was performed, then RNA was collected.

100 μL of chloroform was added into the collected RNA and mixed. The mixture was placed at room temperature for 2-3 minutes, then centrifugal separation (13,000 rpm, 15 min, 4° C.) was carried out, and the supernatant was collected. An equal volume of isopropanol was added into the supernatant and mixed thoroughly by gentle inversion. After being placed at room temperature for 10 minutes, centrifugal separation (13,000 rpm, 10 min, 4° C.) was carried out, then the supernatant was decanted. Washing the pellet by addition of 70% of ethanol, centrifugal separation (13,000 rpm, 5 min, 4° C.) was carried out, and the supernatant was decanted. After drying the pellet at room temperature, the pellet was dissolved by adding 20 μL of DEPC water, and the obtained solution was used as a sample.

(2) RT-PCR

RT-PCR was carried out by using ReverTra Ace (R) kit (TOYOBO) and 2×GoTaq (R) Green Master Mix (Promega).

Firstly, the sample prepared in the above-mentioned (1) was diluted up to 250 ng/μL by adding DEPC water. The composition of Table 2 was prepared with using the diluted sample, then treated by thermal cycler with the following steps 1-3 (Step 1: 30° C., 10 min; Step 2: 42° C., 60 min; Step 3: 95° C., 5 min), and cDNA (complementary DNA) was synthesized.

TABLE 2

| | |
|---|---|
| 5x RT Buffer | 4 |
| 2.5 mM dNTP | 8 |
| Oligo (dT) | 1 |
| N—F H$_2$O | 2 |
| RNase inhibitor | 0.5 |
| RTase | 0.5 |
| Sample (250 ng/μL) | 4 |
| Total (μL) | 20 |

Using the synthesized cDNA as a template, and using primers that amplifies each gene shown in Table 3 (β-actin, Smad4, c-myc) and primers that amplifies 18SrRNA as a endogenous control, the composition of Table 4 was treated by thermal cycler with the following steps 1-3 (Step 1: 95° C., 5 min; Step 2: 1) 95° C., 30 sec, 2) 56° C., 40 sec, 3) 72° C., 1 min; with 1)-3) as one cycle, 23 cycles for 18SrRNA and β-actin or 31 cycles for Smad4 and c-myc; Step 3: 72° C., 5min), and DNA was amplified.

The amplified DNA was electrophoresed with agarose gel and dyed with ethidium bromide, then the gel was photographed by E-Graph (ATTO). Semi-quantitative analysis was performed by quantifying fluorescence intensity of each band using ImageJ. As shown in FIG. 5 to FIG. 7, c-myc (FIG. 6) and Smad4 gene expression levels (FIG. 7) were hardly decreased by addition of the extract from the samples cultured in the dark and under blue-light irradiation; however, ca. 25% of the β-actin gene expression level was suppressed by addition of the extract (2% v/v) from the sample irradiated by blue light (FIG. 5).

TABLE 3

| SEQ ID NO. | Gene | Number of Cycles | Sequence |
|---|---|---|---|
| 1 | 18srRNA-F | 23 | AAACGGCTACCACATCCAAG |
| 2 | 18srRNA-R | 23 | CCTCCAATGGATCCTCGTTA |
| 3 | β-actin-F | 23 | AGGTCATCACCATTGGCAAT |
| 4 | β-actin-R | 23 | ACTCGTCATACTCCTGCTTG |
| 5 | Smad4-F | 31 | TTGCTTCCACTTGAATGCTG |
| 6 | Smad4-R | 31 | CTTCAAAGGGACACCAAAA |
| 7 | c-myc-F | 31 | TTCGGGTAGTGGAAAACCAG |
| 8 | c-myc-R | 31 | CAGCAGCTCGAATTTCTTCC |

TABLE 4

| | |
|---|---|
| master mix | 10 |
| N—F H$_2$O | 8 |

TABLE 4-continued

| | |
|---|---|
| Primer | 1 |
| cDNA | 1 |
| Total (μL) | 20 |

(Gene Expression Analysis by Quantitative RT-PCR of Extract-treated Cancer Cells)

Quantitative RT-PCR Method (Real-time PCR)

The cDNA obtained by the above-mentioned reverse transcription reaction was diluted up to 1/100 and used as a template. The reagent composition and primers used in quantitative RT-PCR are shown in Table 5 and Table 6, respectively.

The Reagent Composition for Real-time PCR

TABLE 5

| | |
|---|---|
| KAPASYBR ®FAST qPCR Master Mix (2x) | 10 |
| Nuclease-Free H$_2$O | 7.2 |
| KAPASYBR ®FAST ROX High (50x) | 0.4 |
| Primer (10 μM) | 0.4 |
| 1/100 cDNA | 2 |
| Total (μL) | 20 |

Primers for Real-time PCR

TABLE 6

| SEQ ID NO. | Gene | Sequence |
|---|---|---|
| 9 | 18srRNA-F | CGGCTACCACATCCAAGGAA |
| 10 | 18srRNA-R | GCTGGAATTACCGCGGCT |
| 11 | FABP5-F | GCTGATGGCAGAAAAACTCAGA |
| 12 | FABP5-R | CCTGATGCTGAACCAATGCA |

The prepared reagent was set in StepOne (R) Real-time PCR System (Applied Biosystems) and quantitatively analyzed by ΔΔCT Method.

As shown in FIG. 8, the FABP5 gene expression was significantly decreased by addition of the extracts from the samples cultured in the dark and under blue-light irradiation, and the effect of the extract from the sample cultured under blue light irradiation is stronger than that from the sample cultured in the dark, where ca. 65% of the FABP5 gene expression was suppressed by addition of the extract (2% v/v) from the sample cultured under blue-light irradiation. This shows that the production of antitumor substances can be increased by blue-light irradiation.

INDUSTRIAL APPLICABILITY

The method for producing useful metabolites found by the present invention makes it possible to efficiently produce industrially useful substances such as shikimic acid from filamentous fungi. In recent years, linked with the demand for the anti-influenza drug Tamiflu, attention of the market to shikimic acid has increased and its price has also increased. However, the yield of the current method for producing shikimic acid is still confined to about 0.3-3% and no alternative method has been found, which renders the supply of Tamiflu unstable during influenza pandemic and this causes a social issue. The method for producing shikimic acid of the present invention is capable of obtaining shikimic acid efficiently by using commercially available and inexpensive materials; further, since it is possible to execute the process only in one step, the method can be performed at a low cost and in short time. Further, the method for producing useful metabolites found by the present invention can also efficiently produce antitumor substances.

The invention claimed is:

1. A method for producing useful metabolites comprising a process of suppressing the growth of filamentous fungi by applying light stimulation to filamentous fungi, and a process of extracting useful metabolites from filamentous fungi; wherein the useful metabolite is shikimic acid, and wherein the light stimulation is a stimulus of light having a center wavelength shorter than 570 nm, thereby the biosynthetic pathway of aromatic amino acids is blocked after shikimic acid is biosynthesized.

2. The method according to claim 1, wherein the light stimulation is a stimulus of blue light and/or a stimulus of light having a photon flux density not less than 11 μmol m$^{-2}$ s$^{-1}$.

3. The method according to claim 1, wherein the light stimulation is applied with intermittent irradiation.

4. The method according to claim 1, wherein the extraction is carried out from filamentous fungi in mycelial state.

5. The method according to claim 1, wherein the filamentous fungus is *Pleurotus ostreatus*.

6. The method according to claim 1, wherein the extraction comprises separation into a water layer and an organic layer using an organic solvent and water, and collection of the water layer.

* * * * *